US011007355B2

(12) United States Patent
Giesing

(10) Patent No.: US 11,007,355 B2
(45) Date of Patent: May 18, 2021

(54) DRUG DELIVERY DEVICES AND METHODS FOR TREATMENT OF BLADDER CANCER WITH OXALIPLATIN

(71) Applicant: TARIS Biomedical LLC, Lexington, MA (US)

(72) Inventor: Dennis Giesing, Lee's Summit, MO (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 16/715,857

(22) Filed: Dec. 16, 2019

(65) Prior Publication Data

US 2020/0114133 A1 Apr. 16, 2020

Related U.S. Application Data

(60) Division of application No. 14/628,900, filed on Feb. 23, 2015, now Pat. No. 10,543,346, which is a continuation of application No. PCT/US2013/057836, filed on Sep. 3, 2013.

(60) Provisional application No. 61/696,027, filed on Aug. 31, 2012.

(51) Int. Cl.
| | | |
|---|---|---|
| *A61M 31/00* | (2006.01) | |
| *A61K 9/00* | (2006.01) | |
| *A61P 35/00* | (2006.01) | |
| *A61K 31/555* | (2006.01) | |
| *A61K 31/282* | (2006.01) | |
| *A61K 45/06* | (2006.01) | |
| *A61K 31/7048* | (2006.01) | |

(52) U.S. Cl.
CPC ......... *A61M 31/002* (2013.01); *A61K 9/0034* (2013.01); *A61K 31/282* (2013.01); *A61K 31/555* (2013.01); *A61K 31/7048* (2013.01); *A61K 45/06* (2013.01); *A61P 35/00* (2018.01); *A61M 2205/04* (2013.01); *A61M 2210/1085* (2013.01); *A61M 2210/1096* (2013.01); *A61M 2210/166* (2013.01)

(58) Field of Classification Search
CPC .. A61K 31/282; A61K 9/0034; A61K 31/555; A61M 31/002; A61P 35/00; A61P 13/10
See application file for complete search history.

(56) References Cited

U.S. PATENT DOCUMENTS

| 6,171,298 B1 | 1/2001 | Matsuura et al. |
| 8,343,516 B2 | 1/2013 | Daniel et al. |
| 8,679,094 B2 | 3/2014 | Cima et al. |
| 8,690,840 B2 | 4/2014 | Lee et al. |
| 8,801,694 B2 | 8/2014 | Lee et al. |
| 9,017,312 B2 | 4/2015 | Lee et al. |
| 9,107,816 B2 | 8/2015 | Lee et al. |
| 2004/0260272 A1 | 12/2004 | Friedman et al. |
| 2009/0149833 A1 | 6/2009 | Cima et al. |
| 2010/0015200 A1 | 1/2010 | McClain et al. |
| 2010/0331770 A1 | 12/2010 | Lee et al. |
| 2012/0203203 A1 | 8/2012 | Lee et al. |
| 2013/0324946 A1 | 12/2013 | Tobias et al. |
| 2014/0276636 A1 | 9/2014 | Lee et al. |
| 2015/0165177 A1 | 6/2015 | Giesing |
| 2015/0182516 A1 | 7/2015 | Giesing |

FOREIGN PATENT DOCUMENTS

| WO | 2006030431 A2 | 3/2006 |
| WO | 2009139984 A2 | 11/2009 |
| WO | 2010151893 A1 | 12/2010 |
| WO | 2012065044 A2 | 5/2012 |
| WO | 2012096985 A1 | 7/2012 |
| WO | 2015026813 A1 | 2/2015 |

OTHER PUBLICATIONS

T. Boulikas, et al., "Designing Platinum Compounds in Cancer: Structures and Mechanisms", 2007, Vo. 5, pp. 537-583/.
Hadaschik, et al., "Paclitaxel and Cisplatin as Intravesical Agents Against Non-Muscle-Invasive Bladder Cancer", BJU Int. 2008, 101 (11): 1347-1355.
Hoshohata, et al., "Medicament Information for Appropriate Use No. 18 Anticancer Agent Oxaliplatin", Japan Medical Journal, 2010, 4498, pp. 36-38.
International Search Report and the Written Opinion of the International Searching Authority for PCT/US2013/057836 dated Feb. 13, 2014.
Lokich, J., "What is the "Best" Platinum: Cisplatin, Carboplatin, or Oxaliplatin?", Cancer Investigation. 19(7), 756-760 (2001).
Office Action issued in Japanese Application No. 2015-530138, dated Sep. 7, 2017 (11) pages.
Powles T. et al., "A Comparison of the Platinum Analogues in Bladder Cancer Cell Lines", Urol. Int., pp. 67-72 (2007).
Raymond, E. et al., "Oxaliplatin: A Review of Preclinical and Clinical Studies, " Annals. of Oncol. 9:1053-71 (1998.
Sakai, et al., "Key Drug in Chemotherapy for Colon Cancer: Oxaliplatin", The Journal of Practical Pharmacy 2007, vol. 58, No. 5, pp. 1876-1880.

(Continued)

*Primary Examiner* — Jonathan S Lau

(74) *Attorney, Agent, or Firm* — Eversheds Sutherland (US) LLP

(57) ABSTRACT

Devices and methods are provided for use in the treatment of bladder cancer by locally administering oxaliplatin into the bladder of a patient to achieve a sustained concentration of oxaliplatin in urine in the bladder sufficient to produce a therapeutic concentration of oxaliplatin in bladder tissue. The oxaliplatin may be delivered into the bladder from an intravesical drug delivery device inserted into the bladder, wherein the device continuously releases the oxaliplatin into the urine in the bladder over an extended period of hours or days.

23 Claims, 11 Drawing Sheets

(56) References Cited

OTHER PUBLICATIONS

Winquist E., et al., "A Phase II Study of Oxaliplatin in Urothelial Cancer", Urol. Oncol. Semin. Original Invest. 23 150-154 (2005).
Li Xinwu et al., "Effect of Intravesical Instillation Capecitabine Combined with-Oxaliplatin on the Recurrence of Bladder Cancer", Anti-Tumor Pharmacy, vol. 1, No. 3, Jun. 1, 2011, pp. 203-205 (Abstract).
S. Yokoo, et al., "Significance of Organic Cation Transporter 3 (SLC22A3) Expression for the Cytotoxic Effect of Oxaliplatin in Colorectal Cancer," The American Society for Pharmacology and Experimental Therapeutics vol. 36. No. 11, pp. 2299-2306 (2008).
S. Zhang, et al., "Organic Cation Transporters Are Determinants of Oxaliplatin Cytotoxicity," Cancer Res. 2006; 66: (17). Sep. 1, 2006. pp. 8847-8857—www.aacrjournalts.org.
Zhang, S., et al., "Handbook of Clinical Pharmacology and Application of New Drugs", Chemical Industry Press, pp. 671-676 (Sep. 30, 2007).

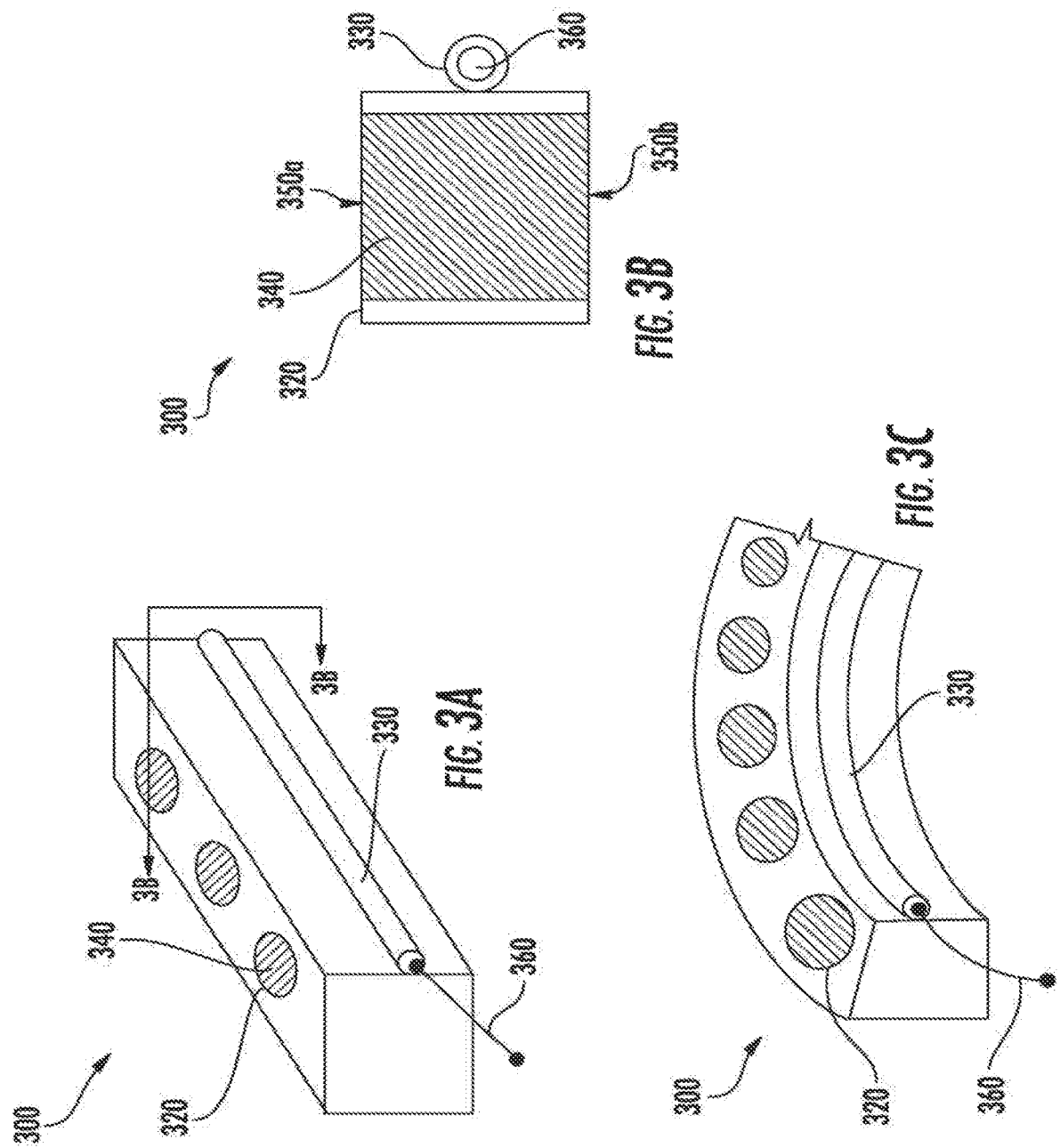

DRUG DELIVERY DEVICES AND METHODS FOR TREATMENT OF BLADDER CANCER WITH OXALIPLATIN

CROSS-REFERENCE TO RELATED APPLICATIONS

This application is a divisional of U.S. patent application Ser. No. 14/628,900, filed Feb. 23, 2015, which is a continuation of PCT/US2013/057836, filed Sep. 3, 2013, which claims priority to U.S. Provisional Patent Application No. 61/696,027, filed Aug. 31, 2012, all of which are incorporated herein by reference.

BACKGROUND

This disclosure is generally in the field of pharmaceutical agents for use in treating the bladder, and more particularly to drug delivery systems, methods, and drug formulations for targeted treatment of urinary bladder cancer.

Delivery of therapeutic agents to the urinary bladder is difficult. Current practice requires systemic administration using doses which result in significant exposure to healthy tissues and relatively low exposure within the bladder. Frequently the systemic exposure leads to unwanted or harmful side effects which limit the usefulness of the agent in treating bladder disease.

To avoid systemic effects, drugs may be delivered locally onto tissues at or near the target tissue. However, such local administration may not be well tolerated by the tissue at the delivery site and/or may not be sufficiently permeable to the particular drug being delivered. Accordingly, there is a need to provide a therapeutic agent that is well tolerated by the bladder when the agent is applied at concentrations effective to achieve sufficient therapeutic (i.e., cytotoxic) concentrations within the target tissues.

Accordingly, there remains a need for improved drug delivery methods and systems for treating the bladder, such as in the treatment of bladder cancer, whether as neoadjuvant therapy, adjuvant therapy, or palliative therapy.

SUMMARY

In one aspect, a medicament is provided that includes oxaliplatin for use in the treatment of bladder cancer by locally administering oxaliplatin into the bladder of a patient to achieve a sustained concentration of oxaliplatin in urine in the bladder sufficient to produce a therapeutic concentration of oxaliplatin in bladder tissue. The locally administering into the patient's bladder may be continuous or intermittent. In one embodiment, the oxaliplatin is delivered into the bladder from an intravesical drug delivery device inserted into the bladder, and the device continuously releases the oxaliplatin into the urine in the bladder over a sustained period. In an alternative embodiment, the oxaliplatin is delivered into the bladder from a coating substance applied to the bladder, which coating substance continuously releases the oxaliplatin into the urine in the bladder over a sustained period. The coating substance may include a mucoadhesive formulation. In a further alternative embodiment, a liquid form of the oxaliplatin is pumped into the bladder through a urethral catheter inserted into the bladder. In various embodiments, the oxaliplatin is released into the patient's bladder continuously over a period of at least 2 hours, such as from 1 day to 14 days. In an embodiment, the oxaliplatin is released into the patient's bladder at a mean average amount of from 1 mg to about 100 mg oxaliplatin per day for 1 day to 14 days. In an embodiment, the oxaliplatin is released into the patient's bladder at a mean average amount of from 1 mg to about 100 mg oxaliplatin per day for up to 7 days.

In another aspect, a medical device is provided for intravesical administration of oxaliplatin. In an embodiment, the device includes a housing configured for intravesical insertion, and a dosage form comprising oxaliplatin, wherein the housing holds the dosage form and is configured to controllably release the oxaliplatin into the bladder in amount therapeutically effective for the treatment of bladder cancer. In an embodiment, the device comprises is elastically deformable between a retention shape configured to retain the device in a patient's bladder and a deployment shape for passage of the device through the patient's urethra. In an embodiment, the device is configured to release from 1 mg/day to 100 mg/day of oxaliplatin for up to 7 days.

In still another aspect, a method is provided for administering oxaliplatin to a patient in need of treatment of bladder cancer. The method includes locally administering oxaliplatin into the bladder of a patient to achieve a sustained concentration of oxaliplatin in urine in the bladder sufficient to produce a therapeutic concentration of oxaliplatin in bladder tissue. The method may further include administering at least a second therapeutic agent to the patient. Non-limiting examples of second therapeutic agents include gemcitabine or another cytotoxic agent; an analgesic agent; an anti-inflammatory agent; or a combination thereof. The second therapeutic agent may be administered intravesically and/or by other routes of administration.

BRIEF DESCRIPTION OF THE DRAWINGS

FIGS. 3A-3C illustrate still another embodiment of an intravesical drug delivery device that may be used for administering oxaliplatin as described herein.

DETAILED DESCRIPTION

Figure 1A:
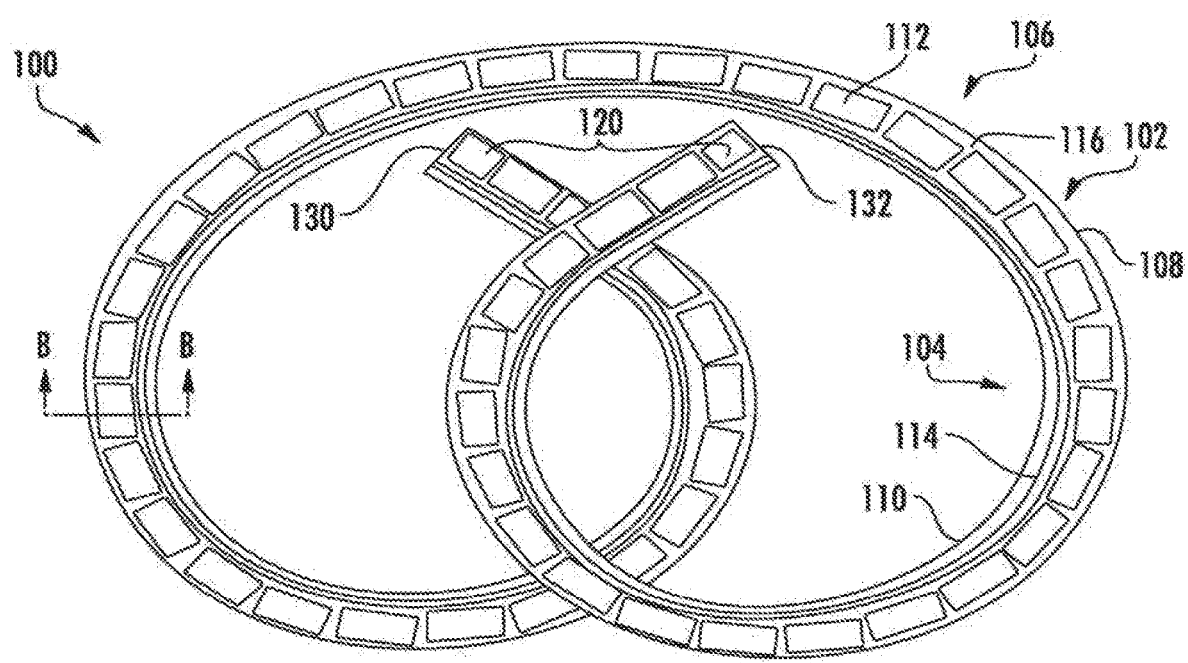
FIGS. 1A-1B illustrate one embodiment of an intravesical drug delivery device that may be used for administering oxaliplatin as described herein.

It has been discovered that intravesical administration of oxaliplatin can be used to achieve therapeutically effective amount of the drug in the tissues where needed and also is well tolerated by the bladder tissue. That is, oxaliplatin was unexpectedly shown to meet both the tissue permeability criteria and the urothelium tolerability criteria when administered into the bladder. Several other drugs tested failed to achieve both. Furthermore, by local, intravesical administration of the oxaliplatin, systemic exposure to the drug is advantageously minimized.

Accordingly, the present methods and devices for treating bladder cancer include locally administering oxaliplatin into the bladder of a patient to achieve a sustained concentration of oxaliplatin in urine in the bladder sufficient to produce a therapeutic concentration of oxaliplatin in bladder tissue.

As used herein, the term "bladder tissue" refers to the bladder wall or one or more layers thereof (e.g., mucosa, muscle, and submucosa).

The term "patient" as used herein refers to humans or other mammals, such as in veterinary or livestock applications, in need of treatment. In a particular embodiment, the patient is an adult human.

Oxaliplatin is platinum-based antineoplastic agent. It is known for use in chemotherapy, for example in the treatment of colorectal cancer, where it is formulated for intravenous administration, e.g., Eloxatin™ (Sanofi-Aventis). In the present invention, the oxaliplatin is formulated for local delivery. It may be provided in solid or semi-solid form or in a liquid form, depending on the delivery mechanism employed, as described herein. Oxaliplatin and methods of manufacture thereof are described, for example, in U.S. Pat. Nos. 5,338,874; 5,420,319; 5,716,988; and 5,290,961.

A variety of methods can be used to achieve the required urine (and thus tissue) concentrations of the oxaliplatin. In one embodiment, the oxaliplatin can be provided by direct instillation of a simple solution into the bladder. For example, a solution of the oxaliplatin may be pumped into the bladder through a urethral or suprapubic catheter in a continuous or pulsatile manner over the treatment period. In another embodiment, the oxaliplatin is released from a device or composition deployed in the bladder, wherein the device or composition releases the oxaliplatin (continuously or intermittently) at a rate effective to produce the desired concentration of drug in the urine over a specified treatment period. At the end of the treatment period, the device may be retrieved from the bladder, or it may be eliminated by being resorbed, dissolved, excreted, or a combination thereof.

In a preferred embodiment, the oxaliplatin is administered to the bladder from an intravesical device. A preferred embodiment of an intravesical drug delivery device and methods for deploying those devices into the bladder are described in the following U.S. Patent Application Publications: US 2012/0203203 (Lee et al.); US 2012/0089122 (Lee et al.); US 2012/0089121 (Lee et al.); US 2011/0218488 (Boyko et al.); US 2011/0202036 (Boyko et al.); US 2011/0152839 (Cima et al.); US 2011/0060309 (Lee et al.); US 2010/0331770 (Lee et al.); US 2010/0330149 (Daniel et al.); US 2010/0003297 (Tobias et al.); US 2009/0149833 (Cima et al.); and US 2007/0202151 (Lee et al.).

In embodiments in which the oxaliplatin is delivered from an intravesical drug delivery device, the oxaliplatin may be housed in the device in various forms, which may depend on the particular mechanism by which the device controllably releases the oxaliplatin into fluid (e.g., urine) in the bladder. In some embodiments, the oxaliplatin is provided in a solid, semi-solid, or other non-liquid form, which advantageously may facilitate stable storage of the drug before the device is used and advantageously may enable the drug payload of the device to be stored in smaller volume than would be possible if the drug were housed in the form of a liquid solution. In an embodiment the non-liquid form is selected from tablets, granules, semisolids, capsules, and combinations thereof. In one embodiment, the oxaliplatin is in the form of a plurality of tablets, such as mini-tablets described in U.S. Pat. No. 8,343,516, which is incorporated herein in pertinent part. In other embodiments, the oxaliplatin may be housed in a liquid form, such as in a solution with a pharmaceutically acceptable excipient.

An embodiment of a drug delivery device 100 is illustrated in FIG. 1A. The device 100 includes a device body having a drug reservoir portion 102 and a retention frame portion 104. In FIG. 1, the device 100 is shown in a relatively expanded shape suited for retention in the body. Following deployment into the body, the device 100 may assume the relatively expanded shape to retain the drug delivery device in the body cavity or lumen.

For the purposes of this disclosure, terms such as "relatively expanded shape", "relatively higher-profile shape", or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including a linear or elongated shape that is suited for deploying the device through the working channel of catheter, cystoscope, or other deployment instrument positioned in the urethra. In embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. The drug delivery device 100 includes an elastic or flexible device body 106 that defines a drug reservoir lumen 108 (i.e., the drug housing) and a retention frame lumen 110. The drug reservoir lumen 108 is designed to house a drug formulation that comprises the oxaliplatin. In the illustrated embodiment, the drug formulation in the form of a number of solid drug tablets 112. The retention frame lumen 110 is designed to house a retention frame 114 to form the retention frame portion 104. The illustrated lumens 108, 110 are discrete from each other, although other configurations are possible.

Figure 1B:
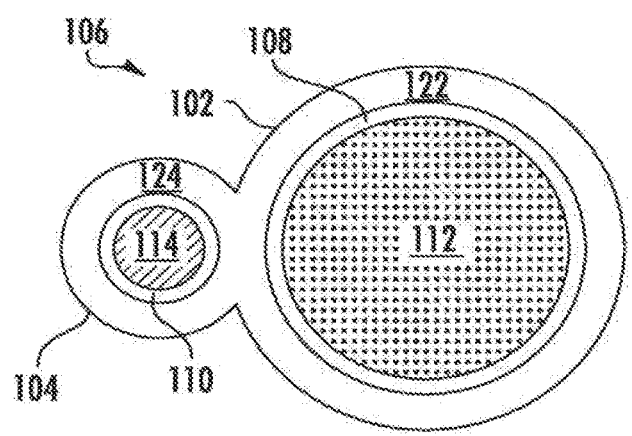

As shown in the cross-sectional view of FIG. 1B, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. The two walls 122, 124 are attached along the entire length of the device in the illustrated embodiment, although intermittent attachment can be employed.

As shown in FIG. 1A, the drug reservoir lumen 108 is loaded with a number of drug units 112 in a serial arrangement. Essentially any number of drug units may be used, for example, depending upon the sizes of the reservoir and the drug units. The drug reservoir lumen 108 includes a first end opening 130 and an opposed second end opening 132. Once the drug units 112 are loaded, restraining plugs 120 are disposed in the openings 130 and 132. The restraining plugs 120, in this embodiment, are cylindrical plugs secured into the entry 130 and the exit 132. In other embodiments, the openings 130 and 132 are closed off with other structures or materials, which may, depending on the particular embodiments, include an aperture or a water- or drug-permeable wall to facilitate ingress or egress of water or drug during use.

The retention frame lumen 110 is loaded with the retention frame 114, which may be an elastic wire. The retention frame 110 may be configured to return spontaneously to a retention shape, such as the illustrated example "pretzel" shape or another coiled shape, such as those disclosed in the applications previously incorporated. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or prevent accidental expulsion.

The material used to form the device body 106, at least in part, may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases.

The material used to form the device body 106 may be water permeable so that solubilizing fluid (e.g., urine or other bodily fluid) can enter the drug reservoir portion 102 to solubilize the drug units 112 once the device is implanted. For example, silicone or another biocompatible elastomeric material may be used. In other embodiments, the device body may be formed, at least in part, of a water-impermeable material.

Figure 2A:
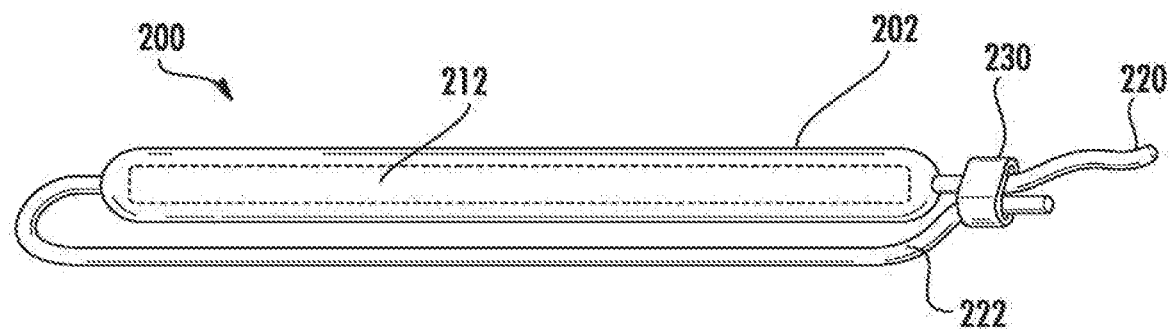
FIGS. 2A-2B illustrate another embodiment of an intravesical drug delivery device that may be used for administering oxaliplatin as described herein.
Figure 2B:
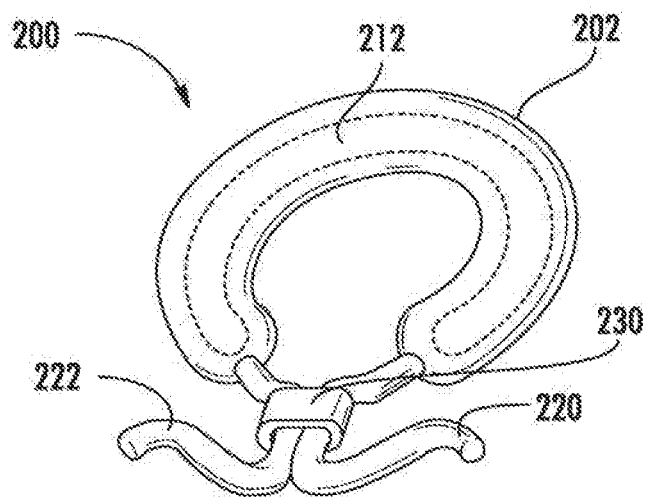

FIG. 2A illustrates an implantable drug delivery device 200, which includes a drug reservoir 202 loaded with drug 212 and a retention structure that includes two filaments 220, 222 associated with a fastener 230. As shown, the drug reservoir 202 is an elongated tube that can be deformed between a relatively linear deployment shape, such as the shape shown in FIG. 2A, and a relatively circular retention shape, such as the shape shown in FIG. 2B. The drug 212 may be loaded in the tube in a flexible form, so that the drug reservoir 102 can be moved between the two shapes. For example, the drug 212 may be a number of solid drug tablets, a liquid, or a gel. The filaments 220, 222 may be attached to opposite ends of the drug reservoir 202 and joined by the fastener 230. The fastener 230 can be adjusted to adjust the position of one filament 220 with reference to the other 222, thereby adjusting the position of one end of the drug reservoir 2102 with reference to the other end. The device 200 can assume the retention shape by adjusting the filaments 220, 222 to draw the ends of the drug reservoir 202 closer together, and thereafter the device 200 can be retained in the retention shape by preventing adjustment of the filaments 220, 222 with the fastener 230. In such an embodiment, the device 200 is manually adjusted into the retention shape by manually adjusting the filaments 220, 222 after the device 200 is inserted into the bladder.

In the illustrated embodiment, the fastener 230 is a cinch nut that permits shortening the portion of the filaments 220, 222 between the drug reservoir ends and the cinch nut, but prevents lengthening of these portions of the filaments 220, 222. Thus, the ends of the drug reservoir 202 can be drawn closer together by pulling one or both of the filaments 220, 222 through the cinch nut, causing the device 200 to assume the retention shape. Once the filaments 220, 222 have been so adjusted, the cinch nut prevents lengthening of the filaments 220, 222, retaining the device in the retention shape. Thus, manually adjusting the device 200 into the retention shape once implanted merely requires pulling one or both of the filaments 220, 222, although other fasteners 230 that require separate manipulation can be employed. Other fasteners may also be used.

Another embodiment of an intravesical drug delivery device is illustrated in FIGS. 3A-3C. In this embodiment, the device includes a housing 300 having a single, continuous structure with multiple, discrete drug reservoir lumens 320 and optionally having at least one retention frame lumen 330 in which a retention frame 360 is disposed. Each drug reservoir lumen 320 has two defined openings, as shown in FIG. 3B, and is dimensioned to hold at least one solid drug unit 340. Solid drug unit 340 may be a drug tablet or capsule. In other embodiments not shown, each drug reservoir lumen has one defined opening. The housing may be formed of a flexible polymer, such as silicone. FIG. 3B is a cross-sectional view of the plane that bisects one of the drug reservoir lumens 320 of the housing shown in FIG. 3A along line 3B-3B. As shown in FIG. 3B, the monolithic housing 300 has two defined openings (350a, 350b) in its drug reservoir lumen 320 that expose both ends of the solid drug unit 340. The retention frame lumen 330, in this embodiment, is aligned parallel to the longitudinal axis of the housing and perpendicular to the drug reservoir lumen 320. FIG. 3C is a perspective view of a portion of the embodiment of the device 300 shown in FIG. 3A when the device is in its retention shape, which is taken when the retention frame 360 is disposed in the retention frame lumen 330. The drug reservoir lumens 320 and the retention frame 360 in the housing of this embodiment are oriented so that the drug reservoir lumens 320 are outside the retention frame's 360 arc. Alternatively, the housing in FIG. 3C can be rotated 180 degrees about the retention frame 360 to yield a configuration in which the drug reservoir lumens 320 are arranged within the retention frame's 360 arc. With this embodiment, the devices provide sufficient direct contact between solid drug units and with urine surrounding the device when deployed and retained in the bladder. In embodiments, release of the drug from the device is controlled by erosion of an exposed portion of the surface of a solid drug unit, such that the rate of drug release from the drug delivery device may be directly proportional to and limited by the total exposed surface area of the solid drug units.

Figure 4A:
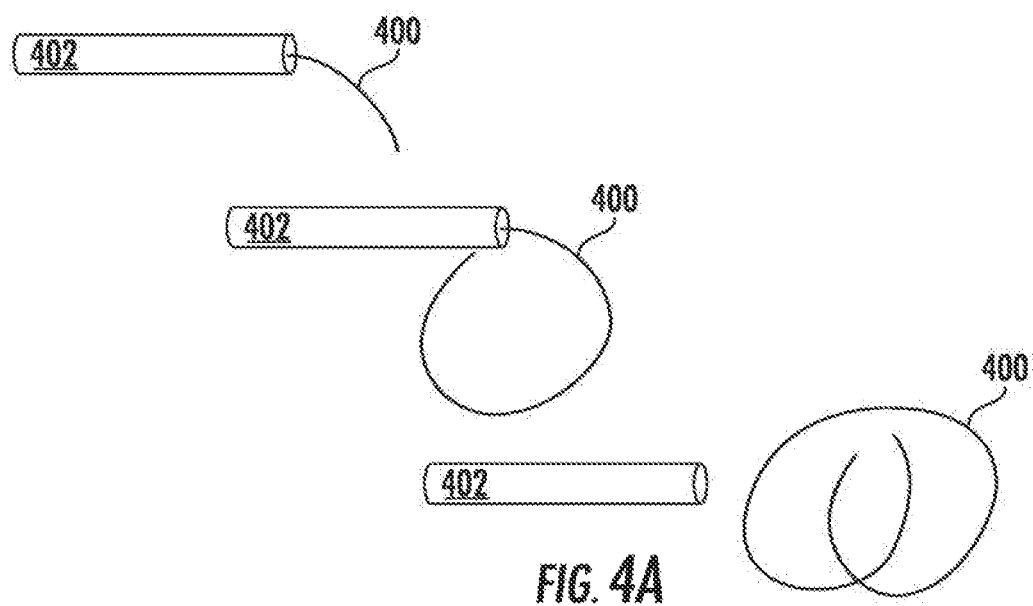
FIGS. 4A-4B illustrate a method of inserting an intravesical drug delivery device into the bladder of a patient for local administration of oxaliplatin as described herein.
Figure 4B:
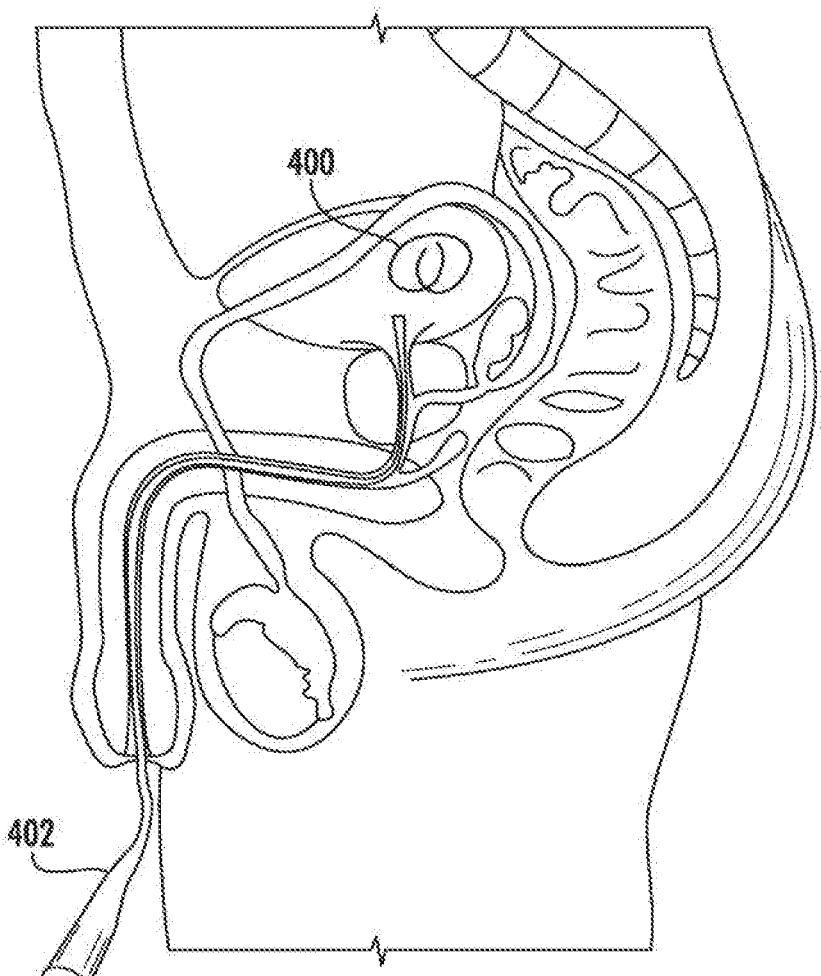

One embodiment of inserting an intravesical device 400 for subsequent controlled release of the oxaliplatin into the bladder is shown in FIGS. 4A and 4B. Here, the device 400 is shown assuming a retention shape as the device exits a deployment instrument 402. The deployment instrument 402 may be any suitable device. It may be a lumenal device, such as a catheter, urethral catheter, or cystoscope. The deployment instrument 402 may be a commercially available device or a device specially adapted for the present drug delivery devices. FIG. 4B illustrates the insertion of the device 400 into the bladder, wherein the adult male anatomy is shown by way of example. The deployment instrument 402 is inserted through the urethra to the bladder, and the device 400 may be passed from/through the deployment instrument 402, driven by a stylet or flow of lubricant or combination thereof until the device 400 exits into the bladder, and as shown is in a retention shape.

In various embodiments, the oxaliplatin may be released from the intravesical drug delivery device by diffusion to through a wall of the drug housing, by diffusion to through one or more defined apertures in a wall of the drug housing, by osmotic pressure through an aperture in the drug housing, by erosion of a drug formulation in contact with urine in the bladder, or by a combination thereof.

In some embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

In various embodiments, the intravesical device may release oxaliplatin continuously or intermittent to achieve a therapeutically effective concentration of oxaliplatin in the bladder tissue over a sustained period, e.g., from 1 hour to 1 month, for example from 2 hours to 2 weeks, from 6 hours to 1 week, from 24 hours to 72 hours, etc.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

In another embodiment, a coating substance may be intravesically applied to the bladder wall, wherein the coating substance includes oxaliplatin and one or more excipient materials that promote adherance of the coating substance to the bladder wall and provides continuous controlled release of the drug over the treatment period. The coating substance may be a mucoadhesive formulation, such as gels, ointments, creams, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof.

Figure 5A:
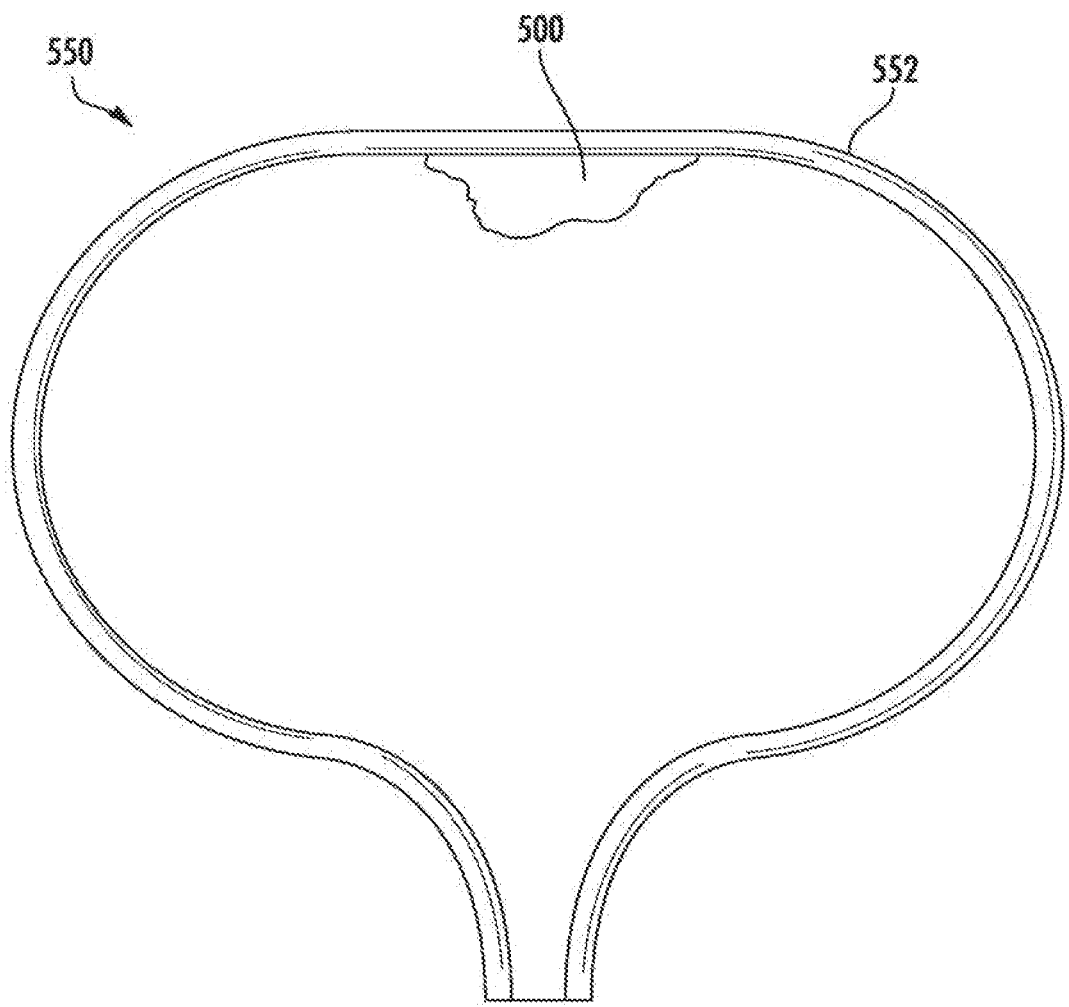
FIG. 5A illustrates a material applied to the inner surface of the bladder wall for local administration of oxaliplatin as described herein.
Figure 5B:
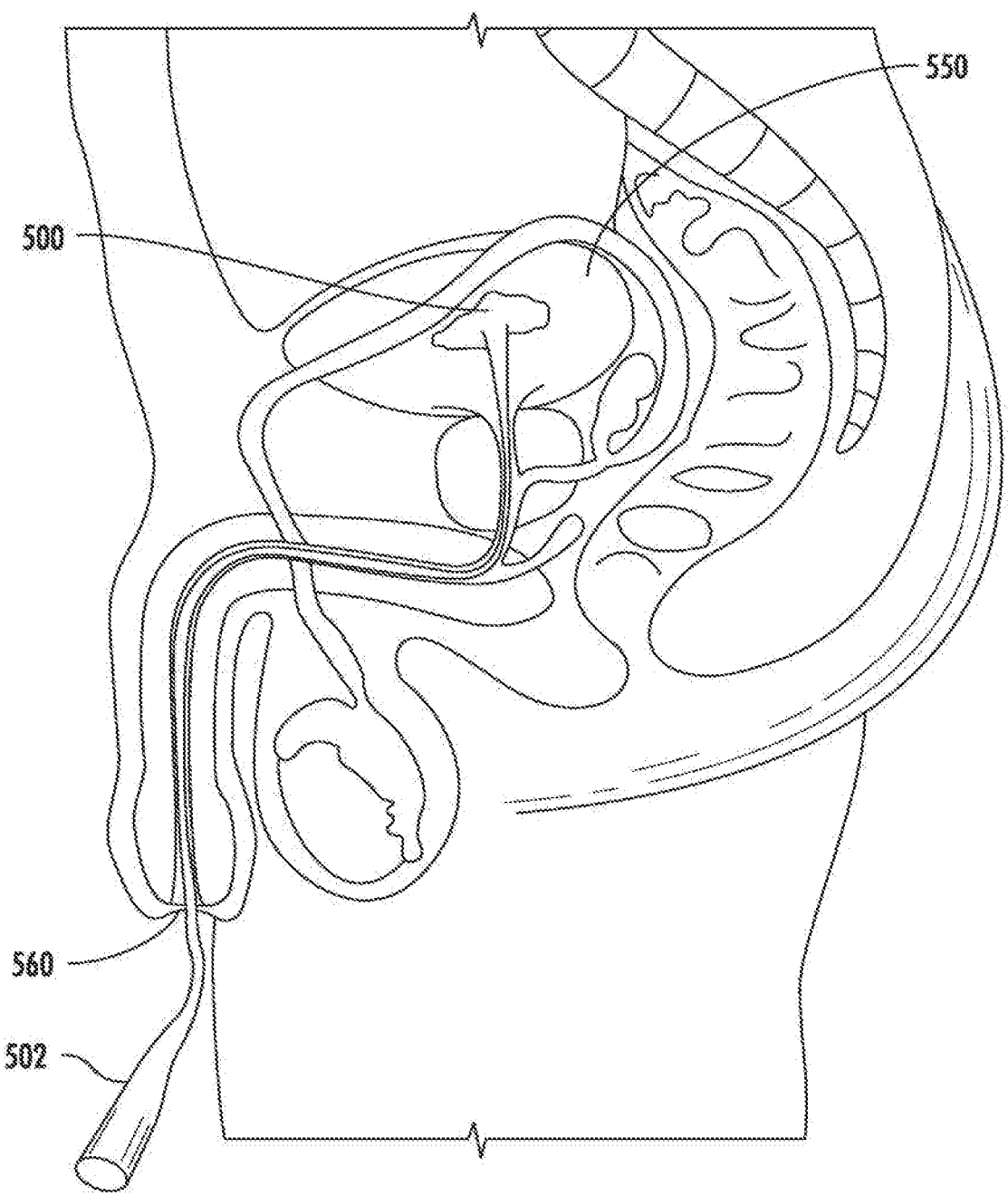
FIG. 5B illustrates a method of applying a coating material onto to the inner surface of the bladder wall for local administration of oxaliplatin as described herein.

As shown in FIG. 5A, a coating substance 500 may be deployed in the bladder 550 so that the coating substance 500 engages/adheres to the bladder wall 552. The coating substance 500 may be deployed in the bladder using a deployment instrument. FIG. 5B is a sagittal view of a male genitourinary system, illustrating a coating substance 500 being deployed through a deployment instrument 502 into the bladder 550. The coating substance 500 may be an embodiment of one of the coating substances described herein. The deployment instrument 502 is sized and shaped for passing through a urethra 560 of a patient to a bladder 550 as shown. The deployment instrument 502 may be a known device, such as a catheter or cystoscope, or a specially designed device. The deployment instrument 502 is used to deploy the coating substance 500 into the bladder and is subsequently removed from the body, leaving the coating substance 500 in the bladder. Once so inserted, the coating substance 500 releases the oxaliplatin into urine and the bladder wall.

The present invention may be further understood with reference to the following non-limiting examples.

Example 1: Testing of Platin Drugs for Bladder Tolerability and Tissue Permeability Two studies were conducted in male Sprague Dawley rats administering cisplatin or carboplatin by intra-urinary bladder cannula, over a 72-hour continuous perfusion, or by a single IV bolus. Blood, urine, and tissue samples were collected and analyzed for drug content. Details of the study design and results are set forth in the tables and description below.

The study protocol was as follows:

|  | Cisplatin | Carboplatin |
| --- | --- | --- |
| Group 1 | 24-hr perfusion via cannula to bladder dome | 24-hr perfusion via cannula to bladder dome |
| Group 2 | 72-hr perfusion via cannula to bladder dome | 72-hr perfusion via cannula to bladder dome |
| Group 3 | Negative control - 72-hr perfusion via cannual to bladder dome | Negative control - 72-hr perfusion via cannual to bladder dome |
| Group 4 | IV bolus with saline perfusion via cannula | IV bolus with saline perfusion via cannula |

For each drug, each test group included three male rats. The perfusate drug concentration was set to 0.3 mg/mL and the perfusion rate used was 300 µL/hour over the test periods.

Details of the study design and results are set forth in the tables and descriptions below.

Perfusion solutions were prepared by dissolving each drug substance into an appropriate volume of saline. The finals doses administered are summarized below.

| Animal # | Compound | Administration Route | Amount Compound Administered via Perfusion Wt. (g) | Actual Dose Administered (mg/kg) |
|---|---|---|---|---|
| 1 (Group 1) | Cisplatin | Bladder Perf. | 6.95 | 2.14 |
| 2 (Group 1) | Cisplatin | Bladder Perf. | 6.88 | 2.12 |
| 3 (Group 1) | Cisplatin | Bladder Perf. | 7.02 | 2.16 |
| 4 (Group 2) | Cisplatin | Bladder Perf. | 20.44 | 6.30 |
| 5 (Group 2) | Cisplatin | Bladder Perf. | 21.20 | 6.53 |
| 6 (Group 2) | Cisplatin | Bladder Perf. | 20.59 | 6.34 |
| 10 (Group 4) | Cisplatin | IV Bolus | 0.9820 | 0.74 |
| 11 (Group 4) | Cisplatin | IV Bolus | 1.0319 | 0.77 |
| 12 (Group 4) | Cisplatin | IV Bolus | 1.1210 | 0.84 |
| 22 (Group 1) | Carboplatin | Bladder Perf. | 7.08 | 2.18 |
| 23 (Group 1) | Carboplatin | Bladder Perf. | 6.87 | 2.12 |
| 24 (Group 1) | Carboplatin | Bladder Perf. | 7.02 | 2.16 |
| 25 (Group 2) | Carboplatin | Bladder Perf. | 20.89 | 6.43 |
| 26 (Group 2) | Carboplatin | Bladder Perf. | 21.22 | 6.54 |
| 27 (Group 2) | Carboplatin | Bladder Perf. | 20.70 | 6.38 |
| 31 (Group 4) | Carboplatin | IV Bolus | 1.1155 | 0.84 |
| 32 (Group 4) | Carboplatin | IV Bolus | 1.1507 | 0.86 |
| 33 (Group 4) | Carboplatin | IV Bolus | 1.1195 | 0.84 |

Whole blood samples were collected at various time points following the start of perfusion, including times 0, 12, 24, 48 and 72 hours as applicable. Urine was collected pre-dose and for 0-24, 24-48, and 48-72-hour periods post dose.

Following the planned infusion periods the animals, terminal blood samples were taken via the abdominal aorta, and the bladder, prostate, ureter, and kidney tissues were collected, weighed, and visually inspected for evidence of drug tolerability.

For animals dosed with cisplatin (Groups 1, 2, and 4), all animals appeared normal during perfusion period except as noted below. Tissue observations at necropsy are also summarized.

| Group Numbers | Clinical Observations of note during Perfusion | Tissue Observations at Necropsy |
|---|---|---|
| Group 1 (Animals 1, 2, 3) | Normal | Bladder lumen: slight to mild erythemic discoloration, 30-50% of lumen, mild to moderate severity, mild edema/thickened bladder walls |
| Group 2 (Animals 4, 5, 6) | Red tinted urine at 72 hrs, all animals | Bladder lumen: generalized erythemic discoloration, 30-50% of lumen, mild to moderate severity, blood clots, moderate edema/thickened bladder walls |
| Group 3-CONTROL (Animals 7, 8, 9) | Dark colored urine (one animal @ 46 hr) | Slight to mild focal erythemia |
| Group 4 (Animals 10, 11, 12) | Normal | No observations |

For animals dosed with carboplatin, all animals appeared normal during perfusion period. Tissue observations at necropsy are also summarized.

| Group Numbers | Clinical Observations of note during Perfusion | Tissue Observations at Necropsy |
|---|---|---|
| Group 1 (Animals 22, 23, 24) | Normal | Bladder lumen: slight to mild generalized erythemic discoloration, 10-30% of lumen, no evidence of tissue edema |
| Group 2 (Animals 25, 26, 27) | Normal | Bladder lumen: slight to mild generalized erythemic discoloration, 10-30% of lumen, no evidence of tissue edema |
| Group 3-CONTROL (Animals 28, 29, 30) | Red tinted urine (one animal) | Bladder lumen: slight generalized erythemic discoloration, 5-10% of lumen, mild tissue edema (one animal) |
| Group 4 (Animals 31, 32, 33) | Red tinted urine (one animal) | Bladder lumen: slight generalized erythemic discoloration, 5-10% of lumen, no evidence of tissue edema |

Figure 6:
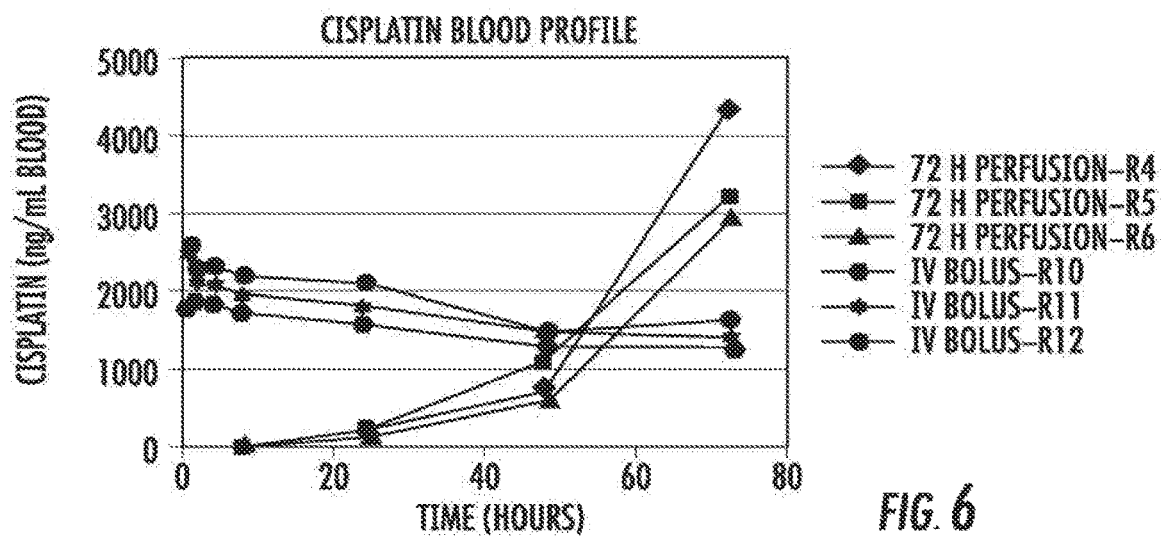
FIG. 6 is a graph of cisplatin blood profile from a study administering the drug by IV bolus or intra-bladder perfusion in rats.
Figure 7A:
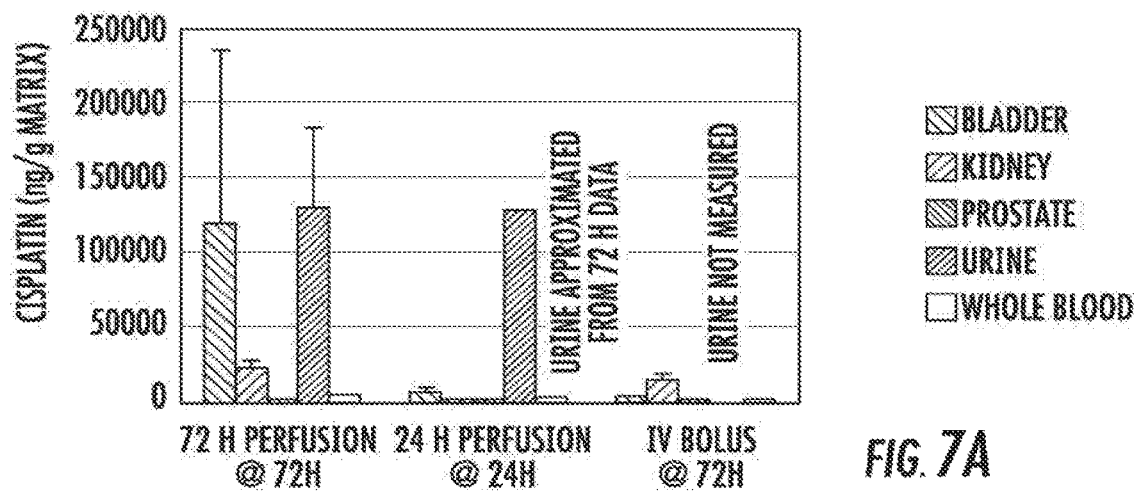
FIGS. 7A-7C are graphs of cisplatin terminal concentrations in blood, urine, and tissue samples from a study in rats.
Figure 7B:
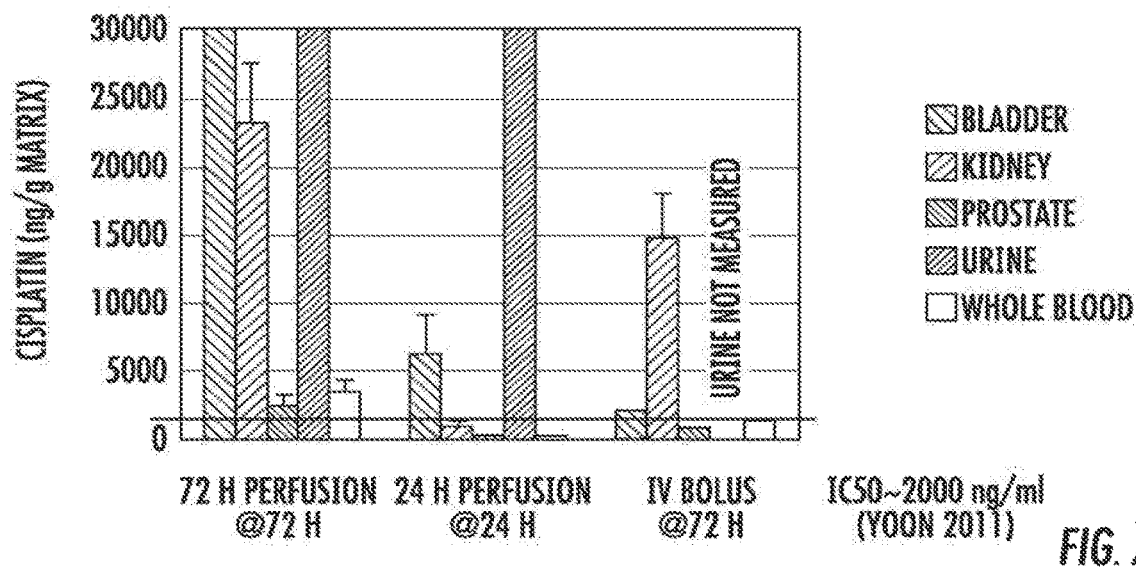

Gross pathology observations were substantiated by tissue histology. ICP-MS for platinum was used to test (i) serial whole blood, (ii) daily urines in 24-hr collections, and (iii) terminal tissues, including bladder, kidney, and prostate. FIG. 6 is a graph showing the blood profile for cisplatin. The 72 h group show rising blood levels suggesting degradation of the bladder lumen permitting increased tissue cisplatin uptake. FIGS. 7A and 7B are graphs showing cisplatin terminal concentrations in the various tissue and fluid samples. Significantly higher and more variable bladder platinum concentrations were observed following 72 hr perfusions when compared to 24 hr perfusions and were associated with the pronounced bladder tissue toxicities observed at necropsy. Individual 72 hr bladder concentration values were 12,000 ng/g, 60,000 ng/g and 160,000 ng/g.

IV bolus administration resulted in measurable kidney and bladder tissue platinum levels at 72 hr despite low urine concentrations. In the IV dosing group kidney to bladder platinum concentration ratio was the inverse of that observed following bladder perfusion. Kidney tissue concentration was highest, followed by the bladder concentration both of which were achieved at approximately half the plasma concentrations observed at 72 h. Increased bladder concentration observed following perfusion may reflect absorption by bladder from both systemic (blood) and urine (urinary clearance) of platinum (which is also supported by elevated kidney levels).

Figure 7C:
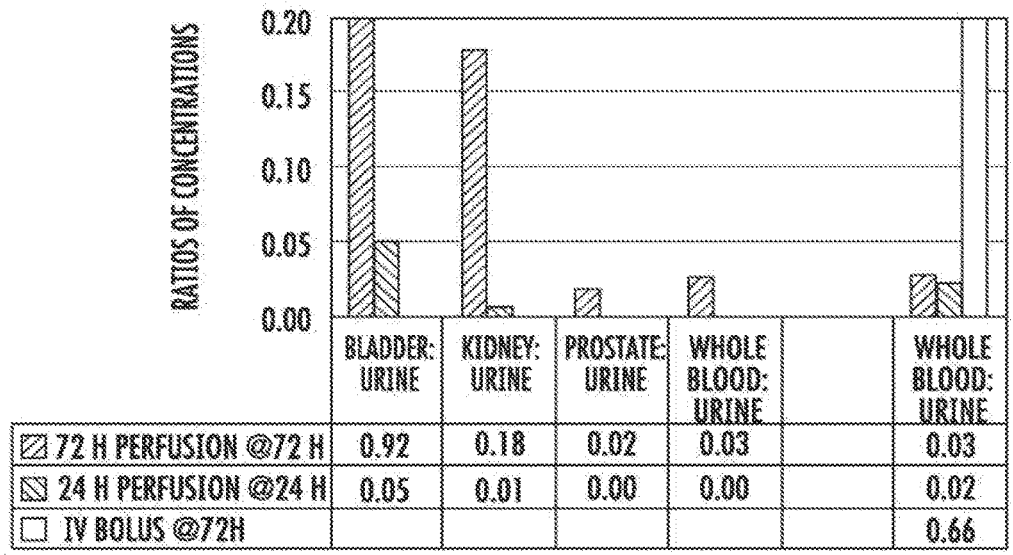

FIG. 7C is another graph showing cisplatin terminal concentrations. The bladder:urine ratio was near 100% for the 72 hr perfusion (tox). The bladder:urine ratio was 5% for the 24 hr perfusion, which reflects cisplatin partitioning when the urothelium is less damaged, exhibiting only mild to moderate erythema as observed in the 24 hr necropsy results (Group 1). For whole blood, the bladder ratio was 66% at 72 hr for the IV bolus administration due to the long half-life of platinum compounds when administered systemically. These results confirm a significant advantage of intravesical bladder perfusion when the urothelium is largely intact. Significant bladder levels can be attained without meaningful systemic exposure.

Figure 8:
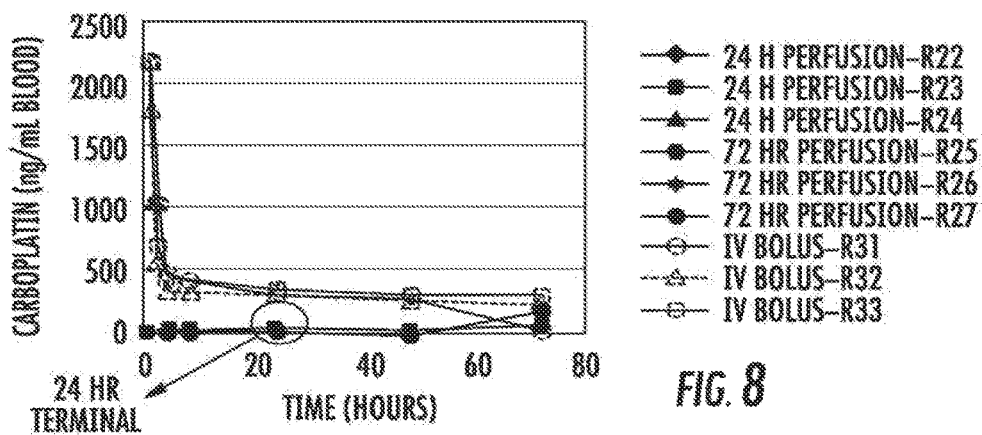
FIG. 8 is a graph of carboplatin blood profile from a study administering the drug by IV bolus or intra-bladder perfusion in rats.

FIG. 8 is a graph showing the blood profile for carboplatin. Observed plasma levels were near the limit of the assay detection (twice the limits of detection) to below the quantitation limit were observed for the perfusion groups. The IV bolus shows significant peak systemic platinum exposure followed by a sharp decay (faster clearance than observed with cisplatin). There was one quarter less carboplatin in the IV bolus terminal phase as compared with cisplatin.

Figure 9:
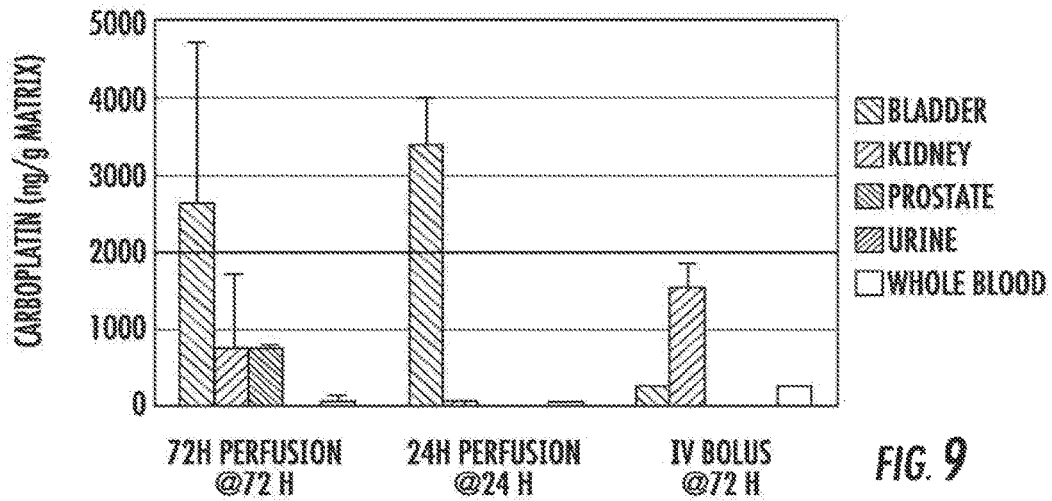
FIG. 9 is a graph of carboplatin terminal concentrations in blood, urine, and tissue samples from a study in rats.

FIG. 9 is a graph showing carboplatin terminal concentrations in the various tissue and fluid samples. Note the scale difference compared to FIG. 6. Carboplatin tissue levels were observed to be consistently less than those observed following cisplatin bladder perfusion. In the bladder, tissue concentrations were below the $IC_{50}$ of carboplatin. The findings suggest intravesical perfusion of carboplatin does not achieve therapeutic tissue platinum concentrations.

Example 2: Oxaliplatin Screening for Bladder Tolerability and Tissue Permeability A study was conducted in male Sprague Dawley rats administering oxaliplatin, oxybutynin, trospium, or tolterodine by intra-urinary bladder cannula, over a 72-hour continuous perfusion. Blood, urine, and tissue samples were collected and analyzed for drug content. Details of the study design and results are set forth in the tables and descriptions below.

| Animal # | Compound | Administration Route | Amount Compound Administered via Syringe Wt. (g) | Actual Dose Administered per animal based on syringe Wt. (mg/kg) |
|---|---|---|---|---|
| 47 | Oxaliplatin | Bladder Perf. | 21.28 | 6.55 |
| 48 | Oxaliplatin | Bladder Perf. | 21.06 | 6.49 |
| 49 | Oxaliplatin | Bladder Perf. | 22.29 | 6.37 |

Clear solutions of oxaliplatin were prepared in saline vehicle. The perfusate formulation concentration was 0.308 mg/mL. Dose (mg/kg) was calculated as (Dose administered (g) x formulation concentration (mg/mL))/Animal Wt. (kg). The drug solutions were dosed over a 72-hour period into the non-fasted animal's bladder by intra-urinary bladder cannula using an infusion pump. This dose was selected based results observed with carboplatin and cisplatin.

Whole blood samples were taken via tailnick or jugular vein cannula at the following time points following the start of perfusion: 0, 4, 8, 24, and 48 hours. Urine was collected pre-dose and for 0-24, 24-48, and 48-72-hour periods post dose. All animals appeared normal throughout the study.

Following the 72-hour infusion period the animals were sacrificed, terminal blood samples were taken via the abdominal aorta, and bladder, prostate, ureter, and kidney tissues were collected, weighed, and visually inspected for evidence of tolerability/reaction from exposure to the drug. All tissues appeared normal except as noted below:

| Animal # | Observations |
|---|---|
| 47 | Slight erythemia 20% of surface, on inside wall of bladder associated with the bladder cannula mild erythemia noted |
| 48 | Slight erythemia 20% of surface, on inside wall of bladder associated with the bladder cannula moderate erythemia and edema noted |
| 49 | Slight erythemic <5% of surface, otherwise normal urothelium |

Figure 10:
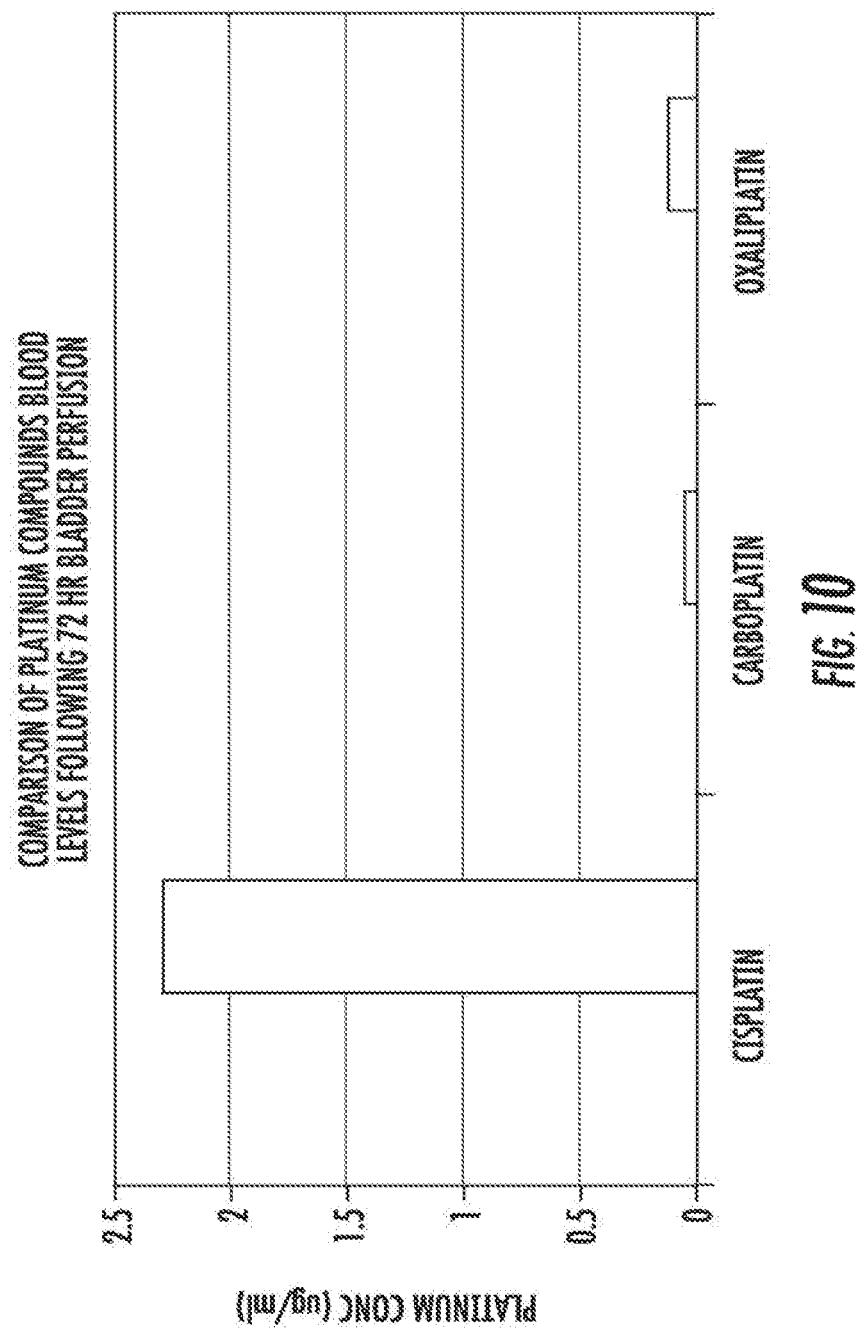
FIG. 10 is a graph showing cisplatin, carboplatin, and oxaliplatin blood levels following 72 hour bladder perfusion in rat study.

FIG. 10 compares the blood profiles for cisplatin, carboplatin, and oxaliplatin. Comparing these graphs, it was observed that oxaliplatin concentrations fell between cisplatin and carboplatin.

Figure 11:
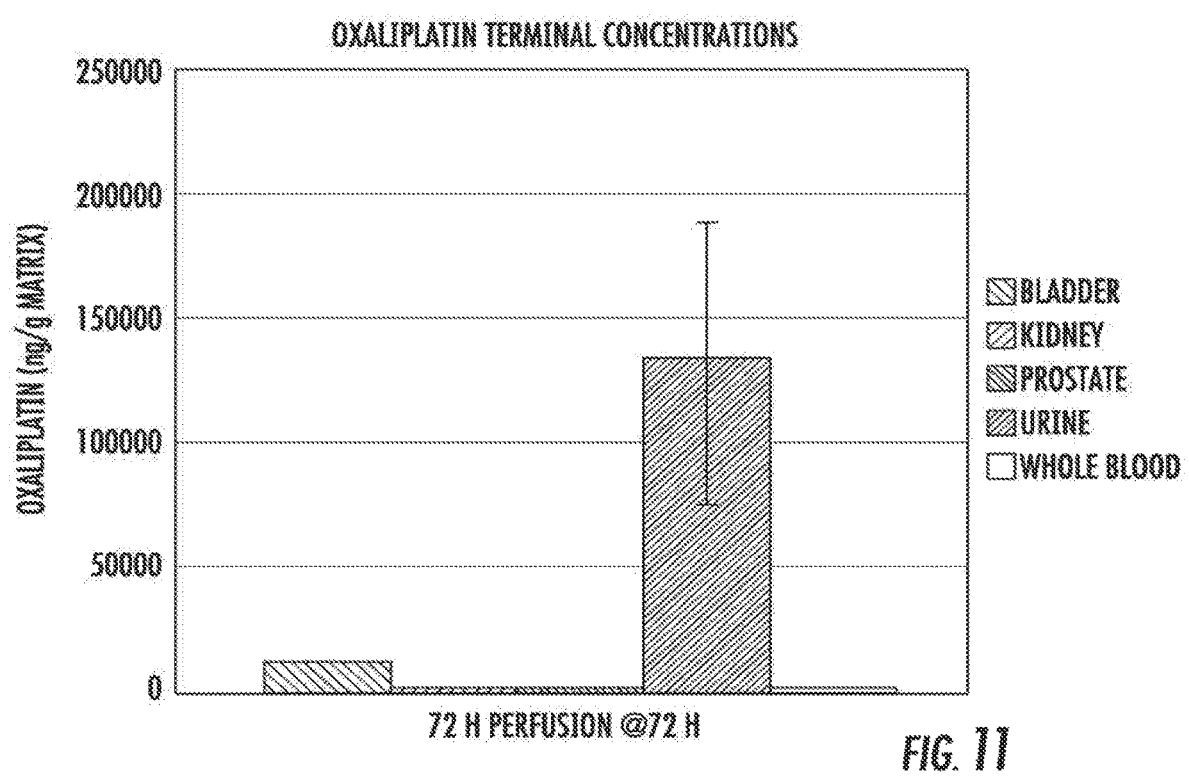
FIG. 11 is a graph showing oxaliplatin terminal concentrations in tissues following 72 hour bladder perfusion in rat study

FIG. 11 graphs of the terminal bladder concentrations for oxaliplatin. Oxaliplatin data showed a bladder:urine ratio of 10%. No appreciable platinum concentration was observed in the kidney or prostate.

Figure 12B:
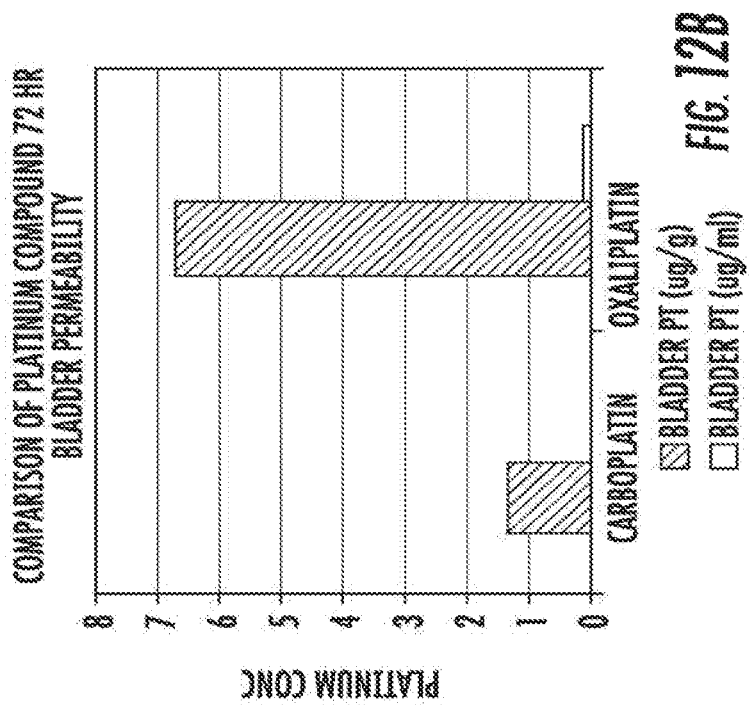
FIGS. 12A-12B are graphs showing cisplatin, carboplatin, and oxaliplatin bladder permeability following 72 hour bladder perfusion in rat study.
Figure 12A:
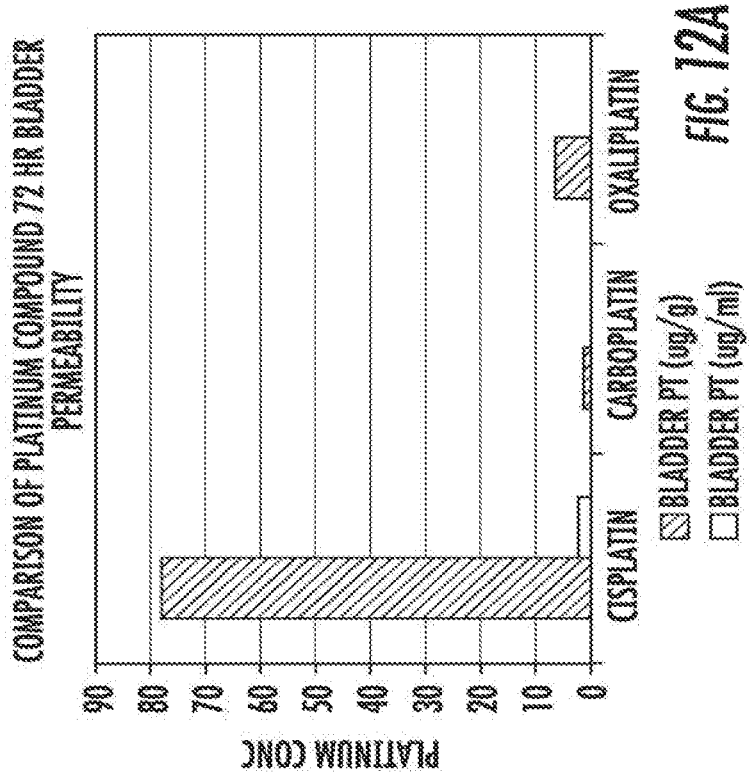

FIGS. 12A and 12B compare bladder platinum concentrations following cisplatin, carboplatin and oxaliplatin bladder perfusion. Surprisingly, oxaliplatin exhibited significant platinum bladder concentrations compared to the trends observed following cisplatin and carboplatin. Comparatively low blood and kidney platinum concentrations were observed in contrast to cisplatin. In comparison to carboplatin, high bladder platinum concentrations were associated with comparably low platinum levels in the blood.

The results surprisingly show both bladder tolerability and tissue permeability for oxaliplatin, but that cisplatin and carboplatin meet only one or other of these criteria (see Example 1).

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A medical device comprising:
a housing configured for intravesical insertion; and
a dosage form comprising oxaliplatin,
wherein the housing holds the dosage form and is configured to release the oxaliplatin into a patient's bladder in amount therapeutically effective for the treatment of bladder cancer.

2. The medical device of claim 1, which is configured to release the oxaliplatin continuously for at least 24 hours.

3. The medical device of claim 1, which is configured to release the oxaliplatin at a mean average amount of from 1 mg/day to about 100 mg/day over a sustained period of from 1 day to 14 days.

4. The medical device of claim 1, which is configured to release the oxaliplatin at a mean average amount of 1 mg/day to about 100 mg/day for up to 7 days.

5. The medical device of claim 1, wherein the dosage form comprising oxaliplatin is a non-liquid form.

6. The medical device of claim 5, wherein the non-liquid form is selected from tablets, granules, semisolids, capsules, and combinations thereof.

7. The medical device of claim 1, wherein the housing is configured to release the oxaliplatin by diffusion through a wall of the housing.

8. The medical device of claim 1, wherein the housing comprises a biocompatible elastomeric material.

9. The medical device of claim 1, wherein the housing comprises a drug reservoir lumen containing the dosage form and the dosage form comprises a plurality of tablets comprising the oxaliplatin.

10. The medical device of claim 1, wherein the housing further comprises a retention frame lumen in which a shape retention frame is disposed.

11. The device of claim 1, wherein the housing comprises an aperture through which the oxaliplatin is configured to be released by osmotic pressure.

12. The device of claim 1, wherein the housing is elastically deformable between a retention shape configured to retain the device in the patient's bladder and a deployment shape for passage of the device through the patient's urethra.

13. An intravesical drug delivery device comprising:
a device body comprising:
a retention frame lumen housing a retention frame; and
a drug reservoir lumen housing a dosage form comprising oxaliplatin, wherein the device is configured to release the oxaliplatin continuously over a period of at least 24 hours.

14. The intravesical drug delivery device of claim 13, wherein the dosage form is selected from tablets, granules, semisolids, capsules, and combinations thereof.

15. The intravesical drug delivery device of claim 13, which is configured to release the oxaliplatin at a mean average amount of 1 mg/day to about 100 mg/day for up to 7 days.

16. The intravesical drug delivery device of claim 13, which is configured to release the oxaliplatin at a mean average amount of from 1 mg/day to about 100 mg/day over a sustained period of from 1 day to 14 days.

17. The intravesical drug delivery device of claim 13, wherein the housing is configured to release the oxaliplatin by diffusion through a wall of the housing.

18. The intravesical drug delivery device of claim 13, wherein the housing comprises an aperture through which the oxaliplatin is configured to be released by osmotic pressure.

19. The intravesical drug delivery device of claim 13, wherein the housing is formed of an elastomeric material.

20. The intravesical drug delivery device of claim 19, wherein the housing is elastically deformable between a retention shape configured to retain the device in a patient's bladder and a deployment shape for passage of the device through the patient's urethra.

21. An intravesical drug delivery device for the treatment of bladder cancer comprising:
  an elastomeric device body which comprises a wall defining a drug reservoir lumen, wherein the wall comprises an aperture extending therethrough;
  a drug payload in a solid form disposed in the drug reservoir lumen, the drug payload comprising oxaliplatin,
  wherein the device, when deployed in a patient's bladder, is configured to permit solubilization of the drug payload and provide continuous release of the oxaliplatin at a mean average amount of from 1 mg/day to about 100 mg/day for at least 72 hours and effective to produce a therapeutically effective amount of the oxaliplatin in the bladder tissues.

22. The intravesical drug delivery device of claim 21, wherein the solid form comprises a plurality of tablets.

23. The drug delivery device of claim 20, wherein the device is configured to provide continuous release of the oxaliplatin though the aperture driven by osmotic pressure.

* * * * *